US008129350B2

(12) United States Patent
Lang et al.

(10) Patent No.: US 8,129,350 B2
(45) Date of Patent: Mar. 6, 2012

(54) METHOD OF LOWERING GLYCAEMIC INDEX OF FOODS

(75) Inventors: Timothy Ralston Lang, Chatswood (AU); Michael Gerard O'Shea, Runcorn (AU)

(73) Assignee: Queen Bioactives Pty Ltd, Aderley (AU)

( * ) Notice: Subject to any disclaimer, the term of this patent is extended or adjusted under 35 U.S.C. 154(b) by 1363 days.

(21) Appl. No.: 11/042,831

(22) Filed: Jan. 25, 2005

(65) Prior Publication Data

US 2005/0175674 A1    Aug. 11, 2005

Related U.S. Application Data

(63) Continuation of application No. PCT/AU03/001001, filed on Aug. 7, 2003.

(30) Foreign Application Priority Data

Aug. 7, 2002 (AU) ................................ 2002950627

(51) Int. Cl.
*A61K 31/70* (2006.01)
(52) U.S. Cl. ................................ 514/25; 514/456
(58) Field of Classification Search ................ 514/25, 514/456
See application file for complete search history.

(56) References Cited

U.S. PATENT DOCUMENTS

| 6,096,364 A * | 8/2000 | Bok et al. | 426/590 |
| 6,409,996 B1 * | 6/2002 | Plaschke | 424/59 |
| 2002/0068704 A1 * | 6/2002 | Ziegler | 514/27 |

FOREIGN PATENT DOCUMENTS

| JP | 5 5013-771 A | 1/1980 |
| JP | 07-061927 A | 3/1995 |
| JP | 2002-10753 * | 4/2001 |
| JP | 2002-010753 | 1/2002 |

OTHER PUBLICATIONS

Plant Foods for Human Nutrition, vol. 61, issue 2, pp. 186-192 (2006) Genovese et al.* Chemical Pharamceutical Bulletin, vol. 34, issue 2, pp. 838-844 (1986) Nakayama et al.*
Alternative Medicine Review (2001) found at http://findarticles.com/p/articles/mi_m0FDN/is_2001_Sept/ai_80532258/pg_1?tag=artBody;coll Wynn.*
New Flavonoids from Sugarcane, Mabry et al, J.Nat. Prod, 1984, 47(1), p. 127-130.*
Life Among the Yanomami (Peters) reprinted in 2001, published by Broadview Press, Ltd., p. 99 obtained from http://books.google.com/books?id=oJdWPOMtGxQC&pg=PA99&dq=sugar+cane+eat#PPA99,M1.*
Doberman Pinschers, Gudas et al, 1987, published by Baron's Educational Series, Inc. p. 36-37.*
Foundations of Nursing, White, 2001, published by Delmar (Thomson Learning), p. 334-335.*
Plant Foods for Human Nutrition, vol. 6, No. 4, pp. 187-192 (2006) abstract only is included.*
Diabetologia, 1990, Swanston-Flatt et al, pp. 462-464.*
J. Agric. Food hem., 2001, Stochmal et al, abstract.*
Patent Abstract of Japan, JP 07-061927 A Published Mar. 7, 1995.
Pateant Abstract of Japan, JP 2002-010753 A Published Jan. 15, 2002.
Shimura et al.; "Inhibitory Effects of Flavonoids on Lipase"; 1994; vol. 41; No. 11, p. 847-850.
Kim et al.; "Inhibition of Alpha-Glucosidase and Amylase by Luteolin, A Flavonoid"; Biosci.Biotechnol. Biochem 2000; vol. 64; No. 1, pp. 2458-2461.
Sampson et al.; "Flavonol and Flavone . . . Professionals"; Journal of the American Dietetic Association; 2002; vol. 102, No. 10; pp. 1414-1420.
Derwent Abstract Accession No. 19056C/11, JP 5 5013-771A (San El Chem Ind KK) Jan. 30, 1980.

* cited by examiner

*Primary Examiner* — Kevin E Weddington
(74) *Attorney, Agent, or Firm* — Ladas & Parry LLP

(57) ABSTRACT

A method of delaying digestion by an animal or a human of carbohydrates in food, comprising administering an effective amount of one or more flavonoids to the animal or human in conjunction with the food, wherein the flavonoids are selected from luteolin, apigenin, tricin and their pharmaceutically acceptable analogues and derivatives.

16 Claims, No Drawings

METHOD OF LOWERING GLYCAEMIC INDEX OF FOODS

This application is a continuation of copending International Application PCT/AU2003/001001 filed on Aug. 7, 2003, which designated the U.S., claims the benefit thereof and incorporates the same by reference.

The present invention relates to a method for lowering the Glycaemic Index (GI) of foods.

Glycaemic Index (GI) is a measure of how a given food affects postprandial blood sugar levels. It relates principally to foods that are high in carbohydrates, since proteins and fats have relatively little effect on blood sugar. GI values indicate how quickly the carbohydrates in a given food are broken down in the intestine and converted to blood sugar. Surprisingly, the complex carbohydrates in some foods such as baked potatoes have a higher GI than refined white sugar. GI values are calculated in comparison with the assimilation of either glucose or white bread, which are given arbitrary GIs of 100. Note that the GI of white bread on the glucose scale is 70.

Glycaemic Load (GL) is an extension of the concept of GI. GL is calculated by multiplying GI by the carbohydrate content of a food, expressed in grams, and divided by 100.

Recent studies have shown that the incidence of type 2 diabetes is on the rise, particularly throughout the Western World, but also in Africa and Asia. Studies have also shown that a diet with a high overall GL increases the relative risk of onset of type 2 diabetes by about 1.5 times, or by about 2.4 times when accompanied by a low dietary fibre intake. The risk of coronary heart disease in diabetics has also been directly linked to dietary GL.

The GI, (and hence the GL) of foods may be reduced by slowing the conversion of carbohydrates into blood sugar. One way of doing this is to increase the viscosity of stomach fluids to slow the rate at which carbohydrates are digested. Alternatively, controlling constriction of the pylorus can reduce the rate at which the stomach empties. The viscosity of stomach fluids may be increased by increasing the consumption of dietary fibre, whilst constriction of the pylorus is achieved by the addition of low molecular weight organic acids, such as acetic acid (vinegar) or citric acid (lemon juice), to the diet.

Another means to lower GI is to inhibit the enzymes catalysing the break down of carbohydrate in the intestine. Two enzymes principally responsible for this are α-glucosidase and α-amylase. The activity of these enzymes determines the rate at which glucose is produced from dietary polysaccharides and therefore the rate at which the glucose is absorbed into the blood.

Hyperglycemia is treated by lowering the GI of foods using the drug Acarbose. This drug is a complex oligosaccharide which delays digestion of ingested carbohydrates, by inhibiting intestinal enzymes (α-glucosidases). Acarbose has maximal inhibitory activity against sucrase. Acarbose is also known to inhibit α-amylases.

Flavonoids are naturally occurring compounds found in plants. According to the present invention, some flavonoids have been found to exhibit inhibitory activity against α-glucosidases and α-amylases. Surprisingly, tests have shown that flavonoids and flavonoid analogues and derivatives isolated from the sugar cane plant exhibit inhibitory activity that exceeds that of Acarbose. Typically, flavonoid derivatives obtained from vegetable sources such as sugar cane are flavonoid glycosides. As used herein the term "flavonoid" is taken to include both flavonoids per se and flavonoid analogues and derivatives.

Luteolin, apigenin and tricin are all flavonoids that occur naturally in plants such as wheat, alfalfa and sugar cane. As noted, the present invention relates to both these compounds and to their analogues and derivatives. In one embodiment, the present invention provides a method of delaying digestion by an animal or a human of carbohydrates in food, comprising administering an effective amount of one or more flavonoids to the animal or human in conjunction with the food, wherein the flavonoids are selected from the group consisting of luteolin, apigenin, tricin and their pharmaceutically acceptable analogues and derivatives. In a preferred embodiment of the invention, the one or more flavonoids are administered together with a nutritional fibre supplement. Preferably at least 7 mg of flavonoid is administered for each 50.0 g of carbohydrate in the food.

In a further embodiment of the invention, there is provided a pharmaceutical formulation suitable for oral administration, said formulation comprising an effective amount of one or more flavonoids selected from the group consisting of luteolin, apigenin, tricin and their pharmaceutically acceptable analogues and derivatives, and one or more pharmaceutically acceptable excipients. The pharmaceutical formulation may contain other active ingredients, in addition to lubricants, colouring and flavouring agents, anti-caking agents and fillers and excipients known to the art. The pharmaceutical formulation may be in the form of a tablet, dragee, pill or capsule provided with an enteric coating. Preferably, in addition to the one or more flavonoids, the pharmaceutical formulation contains a nutritional fibre supplement.

In a further embodiment of the invention, there is provided a method of producing an oral pharmaceutical formulation for inhibiting intestinal enzymes, comprising combining an effective amount of one or more flavonoids selected from the group consisting of luteolin, apigenin, tricin and their pharmaceutically acceptable analogues and derivatives, with one or more pharmaceutically acceptable excipients. The one or more flavonoids may also be combined with other active ingredients. Preferably, the one or more flavonoids are combined with a nutritional fibre supplement.

In a further embodiment of the invention, there is provided a food product containing sufficient added amount of one or more flavonoids selected from luteolin, apigenin, tricin and their nutritionally acceptable analogues and derivatives to reduce the glycaemic index of the food product. Preferably, the amount of added flavonoids contained in the food product is at least 7 mg per 50.0 g of carbohydrate in the food. Preferably, the food product also contains a nutritional fibre supplement.

In another embodiment of the invention, there is provided a method for lowering the glycaemic index of a carbohydrate-containing meal, comprising including as part of the meal an effective amount of an extract of sugar cane containing tricin or its nutritionally acceptable analogues and derivatives. Preferably, the extract contains 5% tricin or tricin diglycoside. Preferably, the amount of extract ranges from 0.3 g to 2.0 g per 50.0 g carbohydrate in the meal; more preferably the amount of extract is about 1.0 g per 50.0 g carbohydrate. In a preferred embodiment, the extract is added to the meal during preparation. In a further preferred embodiment of the invention, a nutritional fibre supplement is also added to the meal.

In another preferred embodiment of the invention, there is provided a method for lowering the glycaemic index of a carbohydrate-containing meal, comprising including as part of the meal an effective amount tricin or its nutritionally acceptable analogues and derivatives. Preferably, the amount of tricin or its analogues or derivatives is at least 7 mg per 50.0 g of carbohydrate in the meal; more preferably it ranges from 15 mg to 100 mg per 50.0 g carbohydrate in the meal; still more preferably the amount is about 50 mg per 50.0 g carbohydrate. In a preferred embodiment, the tricin or its analogues or derivatives is added to the meal during preparation. In a further preferred embodiment of the invention, a nutritional fibre supplement is also added to the meal.

EXAMPLE A

In Vitro Assays

In vitro assays have been conducted which demonstrate the effectiveness of luteolin, apigenin and tricin as inhibitors of digestive enzymes. Apigenin and luteolin were purchased from Sigma and tricin was obtained from the Bureau of Sugar Experiment Stations and supplied by Queen Bioactives Pty. Ltd. Solutions of the flavonoids in dimethylsulfoxide were made at a concentration of five mg/ml.

Alpha-Glucosidase Assay

Alpha-glucosidase Type 1 from bakers yeast, substrate (p-nitrophenyl-alpha-D-glucopyranoside) and a control inhibitor, castanospermine were purchased from Sigma. For the assay, enzyme dissolved in 50 mM acetate buffer, pH 4.5 was incubated for 30 min, at 37° C. in the presence of substrate and in the presence vs. absence of inhibitors (flavonoids or castanospermine at various concentrations). The reaction was carried out in 50 mM acetate buffer, pH 4.5. Final concentration of alpha glucosidase was 0.2 U/ml; final concentration of the substrate was 2 mM. Flavonoids concentrations ranged from 7.8 to 500 μg/ml and castanospermine was used at final concentration 1 μg/ml. The reaction was stopped by addition of 0.2 M $Na_2CO_3$ and absorbance was measured at 405 nm. Background absorbance (without enzyme) was subtracted for every flavonoid concentration used. The inhibitory activity was expressed as 100 minus relative absorbance difference between tested samples and controls.

Alpha-Amylase Assay

Alpha-amylase from porcine pancreas, alpha-glucosidase, glucoamylase and substrate (p-nitrophenyl-alpha-maltopentaoside) were purchased from Sigma. In the reaction, alpha-amylase (endo-type enzyme) hydrolysed the substrate into shorter chain glucosides and the auxiliary enzymes (exo-type enzymes) released the chromophore (p-nitrophenol) from the amylase-hydrolyzed malto-polysaccharides. For the assay, alpha-amylase (7.5 U/ml) was added to a substrate solution containing 1 mM p-nitrophenyl-alpha-maltopentaoside, 15 U/ml of alpha-glucosidase and 25 U/ml of glucoamylase in 50 mM HEPES buffer (pH 7.3) containing 3 mM $CaCl_2$ and 40 mM NaCl. The reaction was carried out for 15 min at 37° C. in the presence vs. absence of flavonoids at concentrations ranged from 11.7 to 750 μg/ml. At the end of the incubation, 0.2 M borate, pH 9.8 was added to inactivate the enzymes and liberated p-nitrophenol was measured spectrophotometrically at 405 nm. The relative activity of alpha-amylase was calculated by subtracting reaction blanks containing the substrate, the two axillary enzymes and flavonoids at the same concentrations. The inhibitory activity was expressed as 100 minus relative absorbance difference between tested samples and controls.

In Vitro Results The alpha-glucosidase assay was carried out in optimum conditions and the activity of the enzyme was reduced by 32% in presence of 1, ug/ml of eastanospermine. As demonstrated in Table 1, addition of all three flavonoids to the reaction mixture resulted in a dose-dependent inhibition of the enzyme but tricin was more active than the other two flavonoids. $IC_{50}$ values (concentrations of flavonoids required to inhibit alpha-glucosidase by 50%) were 51.5 μg/ml, 59.4 μg/ml and 12.0 μg/ml for luteolin, apigenin and tricin, respectively (Table 3). At concentration 1.6 mM (=454 μg/ml) all three flavonoids almost completely or completely inhibited alpha-glucosidase.

In the alpha-amylase assay, flavonoids were the only inhibitors used since they could reduce activity of both alpha-amylase and alpha-glucosidase (the control inhibitor would act only on alpha-amylase). As demonstrated in Table 2, all three flavonoids were effective in reducing the activity of alpha-amylase. Luteolin was the most active, inhibiting the enzyme completely even at the lowest concentration tested. The remaining two flavonoids inhibited alpha-amylase dose-dependently, with tricin being more active than apigenin at lower doses. $IC_{50}$ values (concentrations of flavonoids required to inhibit alpha-amylase by 50%) were 5.8 g/ml, 9.9, ug/ml and 16.2 μg/ml for luteolin, tricin and apigenin, respectively (Table 3). At concentration 1.6 mM, all three flavonoids inhibited alpha-amylase completely (Table 3).

Discussion

The assays show dose-dependent inhibition of alpha-glucosidase and alpha-amylase by flavonoids tested in the study. The data additionally show that for all three flavonoids, concentrations lower than 1.6 mM (lower than 454 μg/ml) were sufficient to produce a substantial inhibition of alpha-glucosidase (70-100% inhibition achieved for concentrations 125-250 μg/ml) and that tricin had much greater inhibitory potential than the other two flavonoids tested.

Similarly, lower than 1.6 mM concentrations of luteolin, apigenin and tricin were sufficient to produce complete inhibition of alpha-amylase.

EXAMPLE B

In Vivo Study

Subjects

A group of 10 healthy, non-smoking people, aged between 18-45 years was recruited from the staff and student population of the University of Sydney to participate in the study. People volunteering to participate in the study were excluded if they were overweight, were dieting, had impaired glucose tolerance, were suffering from any illness or food allergy, or were regularly taking prescription medication other than oral contraceptive medication. A group of seven females and three males participated in the study. The average age of the group of study subjects was 22.3 years (range: 18.9-28.7 years) and the group's average body mass index (BMI) score was 21.5 $kg/m^2$ (range: 19.4-24.8 $kg/m^2$). The BMI score is a measure of a person's weight in relation to their height. BMI values between 19-25 $kg/m^2$ are within the healthy weight range.

Bioactive Extract

A bioactive extract containing tricin diglycoside was used in the In Vivo study. The extract was obtained by:
1. 15 litres of dunder was obtained from CSR Sugar, Sarina, Queensland. (Dunder, (or vinasse), is a commercial by-product obtained after sugar cane molasses is fermented with yeast to convert sugars to ethanol).
2. 30 litres of 96% ethanol (EtOH) was added to the dunder, mixed and allowed to settle for 24 hours.
3. 35 litres of the dunder/ethanol solution was filtered using a stainless steel membrane filter to 0.1 micron. This resulted in 33 litres of permeate.
4. The permeate was evaporated to approximately 5 litres and allowed to settle for 24 hours at 4° C. The permeate was then refiltered in preparation for chromatography.
5. Approximately 0.1% acetic acid by volume was added to the permeate before passing the solution over column chromatography (XAD resin). The column was then washed with one bed volume water (plus 0.1% acetic acid) and then eluted in order with 20%, 30% and 40% EtOH/water containing 0.1% acetic acid.

6. The 40% fraction was evaporated dry at low temperature. The fraction contained 68.95 grams total solids, of which 3.75 g (5.4%) was analysed as an unidentified diglycoside of tricin.

Test Foods

Pure glucose sugar (Glucodin® powder, Boots Health Care Company, North Ryde, NSW, Australia) dissolved in 250 ml of water was used as the reference food, and was consumed by each of the 10 subjects on two separate occasions. The four test meals were consumed by each of the 10 subjects on one occasion only. The four test meals and the reference food were fed to the subjects in portions containing 50 grams of available carbohydrate. The weights and nutrient contents of the test portions of the reference food and the four test meals are listed in Table 4. For the purpose of this study, the bioactive extract was assumed not to provide any macronutrients. The extract contained 5 mg of tricin diglycoside per 100 mg extract.

Each portion of the reference food was prepared the day before required by fully dissolving 50 grams of pure glucose sugar in 250 ml of hot water in a heatproof plastic glass, which was then covered with airtight plastic wrap and stored overnight in a fridge. The next morning, each portion of the reference food was taken from the fridge shortly before being served to a subject together with 250 ml of plain water. The required portions of the four test meals were prepared shortly before being served to the subjects. The wheat-based cereal was weighed into a large china bowl and served to the subjects together with a glass of 185.1 grams of reduced-fat milk, a glass of 250 ml of water, and a small plastic container of the bioactive extract. The subjects were also given a spoon and were instructed to consume everything that was served to them at a comfortable pace within 12 minutes. The subjects were free to decide how they would consume the bioactive extract. Some subjects added the extract to the cereal and milk, whereas others poured some water into the extract's container and consumed it like a drink.

Experimental Procedures

Using standard methodology to determine a food's GI value, a portion of the food containing 50 grams of available carbohydrate is fed to 10 healthy people in the morning after they have fasted for 10-12 hours overnight. A fasting blood sample is obtained and then the food is consumed, after which additional blood samples are obtained at regular intervals during the next two hours. In this way, it is possible to measure the total increase in blood sugar produced by that food over a two-hour period. The two-hour blood glucose (glycaemic) response for this test food is then compared to the two-hour blood glucose produced by the same amount of carbohydrate in the form of pure glucose sugar (the reference food: GI value of glucose=100%). Therefore, GI values for foods are relative measures (ie. they indicate how high blood sugar levels rise after eating a particular food compared to the very high blood sugar response produced by the same amount of carbohydrate in the form of glucose sugar).

In this study, the 10 subjects consumed the reference food on two separate occasions and each of the four test meals on one occasion only. Therefore, each subject completed six separate test sessions for this study. For each subject, the reference food was consumed at both the first and last test sessions, and the four test meals were consumed in random order in between.

The day before each test session, the subjects were required to refrain from consuming alcohol the whole day and to abstain from unusual levels of physical activity or food consumption. The night before each test session, the subjects ate a regular evening meal based on a carbohydrate-rich food (other than legumes) and then fasted for 10 hours overnight.

The next morning they reported to the research centre in a fasting condition. A fasting finger-prick blood sample (0.5 ml) was first collected from each subject using a sterile automatic lancet device (Safe-T-Pro®, Boehringer Mannheim GmbH, Mannheim, Germany). After the fasting blood sample was obtained, the subjects were given a fixed portion of the reference food or a test meal, which they consumed together with 250 ml of plain water at a comfortable pace within 12 minutes. A stopwatch was started for each subject as soon as they started eating. The subjects were required to consume everything that was served to them, after which they were required to remain seated at the research centre and refrain from any additional eating or drinking during the next two hours. Additional finger-prick blood samples were taken 15, 30, 45, 60, 90 and 120 minutes after eating had commenced. Therefore, a total of seven blood samples were collected from each subject during each two-hour test session.

Measurement of Blood Glucose Responses

For each subject, the concentration of glucose in the plasma component of each of the seven blood samples collected during each two-hour test session was analysed in duplicate using a glucose hexokinase enzymatic assay (Roche Diagnostic Systems, Sydney, Australia) and an automatic centrifugal spectrophotometric analyser (Roche/Hitachi 912®, Boehringer Mannheim GmbH, Mannheim, Germany). Using the average plasma glucose concentration for each blood sample, a two-hour blood glucose response curve was then constructed for this subject. The area under this two-hour blood plasma glucose response curve (AUC) was then calculated in order to obtain a single number, which expresses the total increase in blood glucose in that subject as a result of ingesting that test meal during the two-hour experimental period. A glycaemic index (GI) value for this test meal was then calculated for that person by dividing the two-hour blood glucose AUC value for the test meal by their average two-hour blood glucose AUC value for the reference food and multiplying by 100 to obtain a percentage score.

$$\text{GI value for test meal (\%)} = \frac{\text{Blood glucose AUC value for the test meal}}{\text{Average AUC value for the equal-carbohydrate portion of the reference food}} \times 100$$

In this way, a GI value for each test meal was calculated for each of the 10 subjects in the study. The final reported GI value for each test food is the average of the 10 individual subjects' GI values. Due to differences in body weight and metabolism, blood glucose responses to the same food vary between different people. The use of the reference food to calculate GI values reduces the variation between the subjects' blood glucose results to the same food arising from these natural differences. Therefore, the GI value for the same food varies less between the subjects than their glucose AUC values for this food.

In Vivo Results

The average two-hour blood glucose values for the 50 gram carbohydrate portions of the reference food (glucose sugar) and the four test meals shown as the change in blood glucose from the fasting baseline level are set out in Table 4 (excluding outliers' results). The reference food produced the largest blood sugar glucose response, followed by the control meal (cereal+(0 g bioactive extract tricin diglycoside)). The addition of 0.3 g bioactive extract (15 mg of tricin diglycoside) to the cereal test meal did not affect the peak blood glucose concentration at 15 minutes, but resulted in lower blood glucose levels at every time point thereafter. The 1.0 and 2.0 g doses of bioactive extract (50 and 100 mg doses of the tricin diglycoside) resulted in slightly lower peak blood glucose concentrations at 15 minutes, but there is little difference in their overall glycaemic effect.

Glycaemic Index Values

The GI value for each test meal varied among the 10 people who participated in the study. This variation in GI values for the same meal between people is normal and is due to a number of factors, such as the different rates at which the subjects ingested the foods, different physical activity and dietary habits, and genetic differences in carbohydrate metabolism. It is standard scientific practice that if any individual subject's GI value for a test food is either greater than the group mean (average) value plus two standard deviations (StDev) or less than the group mean value minus two StDev then that value is classified as an outlier value or unusual observation and removed from the datasheet. One outlier value was found among the 10 subjects' GI values for the test meals with 50 and 100 mg of the bioactive compound. Therefore, the final GI values for these two test meals is the average of nine subjects' GI values. The mean±standard error of the mean (SEM) GI values for the reference food and the four test meals are listed in Table 6.

CONCLUSIONS

Using glucose as the reference food (GI=100), foods with a GI value of 55 or less are currently considered to be low-GI foods (Brand Miller et. al. The glycaemic index solution for optimal health—the new glycaemic revolution (revised edition), Hodder, Sydney 2003). Foods with a GI value between 56-69 have a medium GI rating, and foods with a GI value of 70 or more are high-GI foods. Therefore, in this study, the meal of wheat-based cereal and reduced-fat milk with no added bioactive extract, the control test meal, was found to have a high GI value. The wheat-based cereal meal with 15 mg of added bioactive extract was found to have a medium GI value, and meals with 50 and 100 mg of added bioactive extract were found to have low GI values. The results of this study suggest that the tricin diglycoside in the extract added to the test meals can effectively reduce the glycaemic response to a high-GI meal. The addition of just 0.3 grams of the bioactive extract (containing approximately 15 mg of tricin diglycoside) reduced the GI value of the control meal by 15 units (21%), causing the meal's average GI value to drop from the high to the medium GI category. The addition of one gram of bioactive extract (50 mg of tricin diglycoside) reduced the GI value to the control meal by 26 units (37%), making it a low-GI meal, on average. The largest dose of bioactive extract (100 mg tricin diglycoside) reduced the GI value to the control meal by an average of 18 units (25%). Therefore, increasing the dose of bioactive compound from 50 to 100 mg did not result in a further reduction of glycaemia.

It will be appreciated that various alterations, modifications and/or additions may be introduced to the invention described herein without departing from the spirit or ambit of the invention.

TABLE 1

Inhibition of alpha-glucosidase by flavonoids luteolin, aplgenin and tricin.

| Flavonoid conc. µg/mL | Luteolin | | Apigenin | | Tricin | |
|---|---|---|---|---|---|---|
| | % control | % inhibition | % control | % inhibition | % control | % inhibition |
| 0 | 100.0 | 0.0 | 100.0 | 0.0 | 100.0 | 0.0 |
| 7.8 | 81.4 | 18.6 | 73.5 | 26.5 | 97.7 | 0.3 |
| 15.6 | 60.2 | 39.8 | 74.3 | 25.7 | 26.4 | 73.6 |
| 31.3 | 65.8 | 34.2 | 68.4 | 31.6 | 15.6 | 84.4 |
| 62.5 | 45.7 | 54.3 | 50.4 | 49.6 | 6.4 | 93.6 |
| 125 | 17.9 | 82.1 | 29.5 | 70.5 | 0 | 100.0 |
| 250 | 19.1 | 80.9 | 0.0 | 100.0 | 0 | 100.0 |
| 500 | 0.0 | 100.0 | 0.0 | 100.0 | 0 | 100.0 |

TABLE 2

Inhibition of alpha-amylase by flavonoids luteolin, apigenin and tricin

| Flavonoid conc. µg/ml | Luteolin | | Apigenin | | Tricin | |
|---|---|---|---|---|---|---|
| | % control | % inhibition | % control | % inhibition | % control | % inhibition |
| 0 | 100.0 | 0.0 | 100.0 | 0.0 | 100.0 | 0.0 |
| 11.7 | 0.0 | 100.0 | 81.0 | 19.0 | 40.9 | 59.1 |
| 23.4 | 0.0 | 100.0 | 0.0 | 100.0 | 18.2 | 81.8 |
| 46.9 | 0.0 | 100.0 | 0.0 | 100.0 | 0.0 | 100.0 |
| 93.8 | 0.0 | 100.0 | 0.0 | 100.0 | 0.0 | 100.0 |
| 187.5 | 0.0 | 100.0 | 0.0 | 100.0 | 0.0 | 100.0 |
| 375.0 | 0.0 | 100.0 | 0.0 | 100.0 | 0.0 | 100.0 |
| 750.0 | 0.0 | 100.0 | 0.0 | 100.0 | 0.0 | 100.0 |

TABLE 3

Summary of alpha-glucosidase and alpha-amylase inhibition by luteolin, apigenin and tricin

| Enzyme | $IC_{50}$ concentration (µg/ml) | | | % inhibition at flavonoid concentration 1.6 mM (454 µg/mL) | | |
|---|---|---|---|---|---|---|
| | Luteolin | Apigenin | Tricin | Luteolin | Apigenin | Tricin |
| Alpha-Glucosidase | 51.5 | 59.4 | 12.0 | 96 | 100. | 100 |
| Alpha-amylase | 5.8 | 16.2 | 9.9 | 100 | 100 | 100 |

TABLE 4

The weights and nutrient content of the test portion of the reference food and the four test meals, calculated using manufacturer's data

| Food | Portion Size (g) | Energy (kJ) | Protein (g) | Fat (g) | Available Carbohydrate (g) | Sugars (g) | Fibre (g) |
|---|---|---|---|---|---|---|---|
| Reference Food (glucose sugar) | 50 g glucose | 800 | 0.0 | 0.0 | 50.0 | 50.0 | 0.0 |

TABLE 4-continued

The weights and nutrient content of the test portion of the reference food and the four test meals, calculated using manufacturer's data

| Food | Portion Size (g) | Energy (kJ) | Protein (g) | Fat (g) | Available Carbohydrate (g) | Sugars (g) | Fibre (g) |
|---|---|---|---|---|---|---|---|
| Wheat-based cereal with reduced-fat milk (control meal) | 250 ml water 60.0 g cereal 185.1 g milk | 1200 | 14.4 | 4.3 | 50.0 | 11.5 | 6.4 |
| Wheat-based cereal with reduced-fat milk + 15 mg tricin diglycoside | 60.0 g cereal, 185.1 g milk, 0.3 g extract | 1200 | 14.4 | 4.3 | 50.0 | 11.5 | 6.4 |
| Wheat-based cereal with reduced-fat milk + 50 mg tricin diglycoside | 60.0 g cereal, 185.1 g milk, 1.0 g extract | 1200 | 14.4 | 4.3 | 50.0 | 11.5 | 6.4 |
| Wheat-based cereal with reduced-fat milk + 100 mg tricin diglycoside | 60.0 g cereal, 185.1 g milk, 2.0 g extract | 1200 | 14.4 | 4.3 | 50.0 | 11.5 | 6.4 |

TABLE 5

Change in mean plasma glucose concentration from fasting baseline level (mmol/L)

| TIME (min) | Glucose reference food (average of two meals) | Control Meal (nil bioactive extract) | 0.3 g bioactive extract | 1.0 g bioactive extract | 2.0 g bioactive extract |
|---|---|---|---|---|---|
| 0 | 0 | 0 | 0 | 0 | 0 |
| 15 | 2.68 | 1.26 | 1.04 | 0.95 | 1.17 |
| 30 | 4.17 | 3.09 | 3.15 | 2.89 | 2.88 |
| 45 | 3.56 | 2.85 | 2.20 | 2.07 | 2.62 |
| 60 | 2.48 | 1.87 | 1.19 | 1.25 | 1.59 |
| 90 | 0.66 | 0.42 | 0.15 | −0.10 | 0.16 |
| 120 | −0.45 | 0.08 | −0.09 | −0.24 | −0.30 |

TABLE 6

The mean SEM GI values for the four test meals and the reference food.

| Test Food | GI Value (%) | GI Category |
|---|---|---|
| Test meal with 50 mg tricin diglycoside | 46 ± 5 | Low |
| Test meal with 100 mg tricin diglycoside | 54 ± 4 | Low |
| Test meal with 15 mg tricin diglycoside | 57 ± 7 | Medium |
| Test meal with 0 mg tricin diglycoside | 72 ± 7 | High |
| Reference food (glucose) | 100 ± 0 | High |

The invention claimed is:

1. A method of delaying digestion by an animal or a human of carbohydrates in food, the method including administering an effective amount of a bioactive extract to the animal or human to delay digestion, wherein the bioactive extract comprises a flavonoid selected from the group consisting of:
   (a) tricin or a diglycoside thereof; and
   (b) tricin or a diglycoside thereof in combination with either or both of luteolin and apigenin.

2. A method according to claim 1 wherein the amount of flavonoid administered is at least 7 mg per 50.0 g of carbohydrates in the food.

3. A method according to claim 1 wherein the flavonoid is derived from sugar cane.

4. A method according to claim 1 wherein flavonoid is administered prior to the food.

5. A method according to claim 1 wherein the flavonoid is administered with the food.

6. A method according to claim 1 wherein the flavonoid is administered after the food.

7. A method according to claim 5 wherein the flavonoid is incorporated into the food.

8. A method according to claim 1 wherein the flavonoid is administered with a nutritional fibre supplement.

9. A method of lowering the glycaemic index of a carbohydrate-containing meal the method including administering an effective amount of a bioactive extract to lower the glycaemic index of a carbohydrate-containing meal, said bioactive extract comprising a flavonoid selected from the group consisting of
   (a) tricin or a diglycoside thereof; and
   (b) tricin or a diglycoside thereof in combination with either or both of luteolin and apigenin.

10. A method according to claim 9 wherein the amount of flavonoid is at least 7 mg per 50.0 g of carbohydrate in the meal.

11. A method according to claim 9 wherein flavonoid is added to the meal during preparation of the meal.

12. A method according to claim 9 wherein the flavonoid is contained in a sugar cane extract.

13. A method according to claim 12 wherein the flavonoid contained in the sugar cane extract comprises 5% tricin or a diglycoside thereof.

14. A method according to claim 12 wherein the amount of sugar cane extract ranges from about 0.3 g per 50.0 g of carbohydrate in the meal to about 2.0 g per 50.0 g of carbohydrate in the meal.

15. A method according to claim 12 wherein the sugar cane extract is added to the meal during preparation of the meal.

16. A method according to claim 12 wherein the sugar cane extract is obtained by
  a. mixing one part dunder with two parts 96% ethanol and allowing to settle for 24 hours;
  b. filtering the dunder/ethanol mixture at 0.1 micron to obtain a permeate;
  c. concentrating the permeate by evaporation to approximately 15% of its initial volume, and refiltering the concentrate;
  d. adding approximately 0.1% by volume acetic acid to the filtered concentrate and passing the resulting mixture through a chromatography column loaded with XAD resin;
  e. washing the chromatography column with one bed volume water containing 0.1% v/v acetic acid, followed by successive elution with 20%, 30% and 40% v/v ethanol in water solutions containing 0.1% v/v acetic acid; and
  f. collecting the 40% fraction and evaporating to dryness at low temperature to obtain a sugar cane extract containing about 5% tricin diglycoside.

* * * * *